United States Patent [19]

Schaller et al.

[11] Patent Number: 5,987,157

[45] Date of Patent: Nov. 16, 1999

[54] IMAGE RECONSTRUCTION METHOD FOR A MULTI-ROW DETECTOR COMPUTED TOMOGRAPHY APPARATUS OPERABLE IN A SPIRAL/HELICAL SCAN MODE

[75] Inventors: Stefan Schaller, Erlangen; Thomas Flohr, Uehlfeld; Heinrich Wallschlaeger, Erlangen, all of Germany

[73] Assignee: Siemens Aktiengesellschaft, Munich, Germany

[21] Appl. No.: 08/829,955

[22] Filed: Apr. 1, 1997

[30] Foreign Application Priority Data

Apr. 10, 1996 [DE] Germany ............... 196 14 223

[51] Int. Cl.$^6$ ................................... G06K 9/00
[52] U.S. Cl. .................. 382/131; 382/128; 378/4; 378/19; 378/901
[58] Field of Search .................. 382/128, 131, 382/279; 378/15, 19, 21, 4, 901, 14

[56] References Cited

PUBLICATIONS

"A General Cone–Bean Reconstruction Algorithm," Wang et al., IEEE Trans. on Med. Imaging, vol. 12, No. 3 Sep. 1993, pp. 486–496.

"Practical Cone–Bean Algorithm," Feldkamp et al. J. Opt. Soc. Am. A. vol. 1, No. 6, Jun. 1984, pp. 612–619.

*Primary Examiner*—Matthew C. Bella
*Attorney, Agent, or Firm*—Hill & Simpson

[57] ABSTRACT

In an image reconstruction method for a multi-row detector computed tomography apparatus operable in a helical/spiral scan mode, a spiral reconstruction with arbitrary pitch and an improvement of the z resolution with interlaced sampling are achieved by using the known Wang reconstruction algorithm expanded by a new type of interpolation technique wherein direct and complementary projections are employed those beams of either the direct or complementary projection always being selected which exhibit the smallest distance in the z-direction from the relevant voxel to be reconstructed.

1 Claim, 5 Drawing Sheets

IMAGE RECONSTRUCTION METHOD FOR A MULTI-ROW DETECTOR COMPUTED TOMOGRAPHY APPARATUS OPERABLE IN A SPIRAL/HELICAL SCAN MODE

BACKGROUND OF THE INVENTION

1. Field of the Invention

The present invention is directed to an image reconstruction method for a multi-row detector computed tomography apparatus operable in a helical/spiral scan mode.

2. Description of the Prior Art

For image reconstruction from data of a simple complete circular revolution of a multi-row detector (MZD) CT scanner, the known Feldkamp algorithm is suitable (see: L. A. Feldkamp, L. C. Davis, J. W. Kress, "Practical cone-beam algorithm," J. Opt. Soc. Am. A, vol. 1, no. 6, June 1984). A generalization of this algorithm by Wang et al. (see: G. Wang, T. H. Lin, P. C. Cheng, D. M. Shinozaki, "A General Cone-Beam Reconstruction Algorithm," IEEE Transactions on Medical Imaging, vol. 12, no. 3, September 1993), can reconstruct images from spiral scans, however, this algorithm has some serious limitations.

Figure 1:
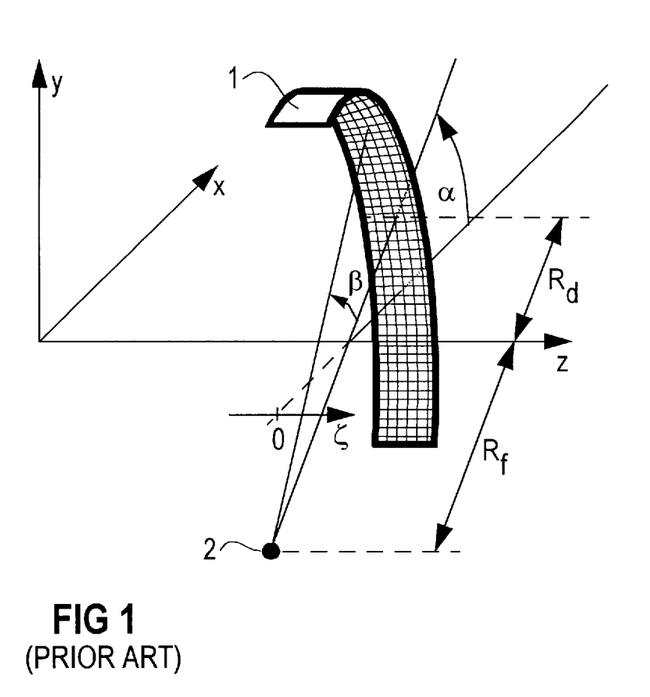
FIGS. 1–3 as noted above, illustrate the known Wang algorithm.

The reconstruction algorithm specified by Wang et al. for a planar detector is formulated herein for the case of a cylindrical detector. FIG. 1 illustrates the construction of the MZD-CT scanner. The multi-row detector 1 is constructed as a cylinder surface. It has several parallel detector rows, each of which is formed from a series of detector elements. The radius of this cylinder is $R_f + R_d$, i.e. the focus 2 is located on the cylinder axis. The focus 2 describes a spiral path with the focus path radius $R_f$. $R_d$ is the distance of the detector 1 to the axis of rotation z. The projection angle (angle of rotation of the gantry with the X-ray source and the detector) is designated $\alpha$. $\beta_m$ and $\zeta_{Det,q}$ identify a particular detector element, and thereby a particular beam from the bundle of rays. $\beta_m$ is the fan angle of the beam, and q is the index of the relevant detector row. The z coordinates of the focus are designated $z_F$, and the spiral has the helical slope slope, described by:

$$z_F = z_{F,O} + n\Delta\alpha \cdot \text{slope} \quad (1)$$

wherein $\Delta\alpha$ is the projection angle increment between successive projections, n is the number of the relevant projection, and $z_{F,O}$ is the z start position of the spiral.

$\zeta_{Det} = z - z_F$ specifies the axial position of a point on the beam in relation to the focus, of which point the projected distance from the focus in the x-y plane is already $R_f + R_d$. This is at the same time the z position of the relevant detector element relative to the z position of the focus. The $\zeta_{Det}$ position of the detector row with index q is given by $$\xi_{Det,q} = \left(q - \frac{N_{rows}}{2} + 0.5 + AQ\right)\Delta\xi_{Det}, \quad (2)$$

with $q = 0 \ldots (N_{rows} - 1)$ wherein $\Delta\zeta_{Det}$ is the distance between two detector rows in the z direction $N_{rows}$ is the number of detector rows, and AQ is the alignment in the $\zeta$ direction. The distance, projected into the rotational center, between two detector rows in the z direction $$\Delta\zeta = \frac{R_f}{R_f + R_d}\Delta\zeta_{Det}$$

or the $\zeta$ coordinates projected thereto $$\zeta = \frac{R_f}{R_f + R_d}\zeta_{Det}$$

is also often used. The logarithmized attenuation values, i.e. the line integrals measured by the detectors via the attenuation coefficients of the object, are designated $p(\alpha_n, \beta_m, \zeta_{Det,q})$, or, in abbreviated form, $p(n,m,q)$. Thereby $$\alpha = n\Delta\alpha, \text{ with } \Delta\alpha = \frac{2\pi}{N_{P,2\pi}} \text{ and } n = 0 \ldots (N_P - 1), \quad (3)$$

as well as $$\beta_m = (m + 0.5 + AM)\Delta\beta, m = \frac{N}{2}\ldots\left(\frac{N}{2} - 1\right) \quad (4)$$

wherein $N_{p,2\pi}$ is the number of projections per $2\pi$ revolution, and $N_P$ is the total number of projections present. N is the number of channels in one row of the detector. For simplicity, it is assumed herein that N is even. AM is the alignment in the fan angle.

The reconstruction method according to Wang et al. in the formulation for cylindrical detectors contains the following steps:

1. Weighting and convolution of the projections $$\tilde{p}(n, m, q) = \frac{1}{R_f\Delta\beta}\sum_{m'=-N/2}^{N/2-1} g_{m-m'} \frac{R_f}{\sqrt{R_f^2 + \zeta_q^2}} \cos\beta_{m'} p(n, m', q) \quad (5)$$

wherein $\cos\beta_m$ is the cos weighting of the data in the row direction required in the fan reconstruction. The convolution takes place only along the rows of the projection, i.e. the operation is carried out independently for all q. The convolution kernel $g_m$ is e.g. the known cotangent kernel $$g_m = \Delta\frac{\beta}{4}\int_{(m-\frac{1}{2})\Delta\beta}^{(m+\frac{1}{2})\Delta\beta} g(\beta)\Delta\beta = \frac{\Delta\beta}{4}\left[\cot\left(\left(m + \frac{1}{2}\right)\Delta\beta\right) - \cot\left(\left(m - \frac{1}{2}\right)\Delta\beta\right)\right] \quad (6)$$

and the distribution $g(\beta)$ is defined by $$g(\beta) = 2\pi^2\int|\omega|e^{j2\pi\omega\sin\beta}d\omega = \lim_{\varepsilon\to 0}\begin{cases}\frac{1}{\varepsilon^2}, \text{ for } |\beta| \leq \varepsilon \\ -\frac{1}{(\sin\beta)^2}, \text{ for } |\beta| > \varepsilon\end{cases} \quad (7)$$

2. Weighted back-projections of the convoluted projections

The back-projection following the convolution is described by $$f(x, y, z) = \qquad (8)$$

$$\frac{2}{\pi N_{P,2\pi}} \sum_{N_0=0}^{N_{P,2\pi}-1} \frac{R_f^2}{(R_f + x\cos\alpha_{n_0} + y\sin\alpha_{n_0})^2 + (-x\sin\alpha_{n_0} = y\cos\alpha_{n_0})^2} \cdot$$

$$\tilde{p}(\lambda(x, y, z, n_0)N_{P,2\pi} + n_0\hat{m}(x, y, z, n_0), \hat{q}(x, y, z, n_0))$$

wherein $n_0$ is a summation index that carries out the summation over all projection angles of a complete revolution. As a rule, in a spiral data set there are several different projections at the same projection angle $\alpha_{n_0}$, namely one in each "winding" of the spiral. By this means, for the unambiguous identification of a projection, besides the projection angle determined by $n_0$, the number $\lambda$ of the "winding" containing it is indicated. In general, in the back-projection a voxel of the reconstruction volume lies in several projections with the same $n_0$ (thus the same projection angle), but different $\lambda$. Thus, an index $\lambda$ must be selected that determines the projection to be used for the back-projection of this voxel. In the Wang algorithm, this $\lambda$ is selected so that the focus position of the projection used has the smallest possible distance in the axial direction from the relevant voxel.

The expression $$\frac{R_f^2}{(R_f + x\cos\alpha_{n_0} + y\sin\alpha_{n_0})^2 + (-x\sin\alpha_{n_0} + y\cos\alpha_{n_0})^2}$$

is what is called the $1/r^2$ weighting that is required in the back-projection of the convolved measurement values in the fan reconstruction.

The indices $\hat{m}$ and $\hat{q}$ result from the projection of a voxel $V(x,y,z)$, to be reconstructed, of the reconstruction volume from the focus to the detector. Let the voxel projected to the detector have the coordinates $\hat{B}$ and $\hat{\xi}_{Det}$. The following is then obtained for the indices $\hat{m}$ and $\hat{q}$:

$$\hat{m}(x, y, z, n_0) = \frac{1}{\Delta\beta} \underbrace{\mathrm{atan}\left(\frac{-x\sin\alpha_{n_0} + y\cos\alpha_{n_0}}{R_f + x\cos\alpha_{n_0} + y\sin\alpha_{n_0}}\right)}_{\hat{\beta}} - 0.5 - AM \qquad (9)$$

or, $$\hat{q}(x, y, z, n_0) = \qquad (10)$$

$$\frac{1}{\Delta\xi_{Det}} \underbrace{\frac{R_f + R_d}{R_f + x\cos\alpha_{n_0} + y\sin\alpha_{n_0}}(z - z_F)}_{\hat{\xi}_{Det}} + \frac{N_{rows}}{2} - 0.5 - AQ$$

$\hat{m}$ is thereby independent of $z$. Since the projection of a voxel from the focus into the detector generally does not strike precisely on a detector element, non-integer-number indices also arise in the evaluation of equations (9) and (10). For this reason, in the back-projection an interpolation takes place between the adjacent elements (e.g. four) of the convoluted projection (e.g.: bilinear interpolation).

Figure 2:
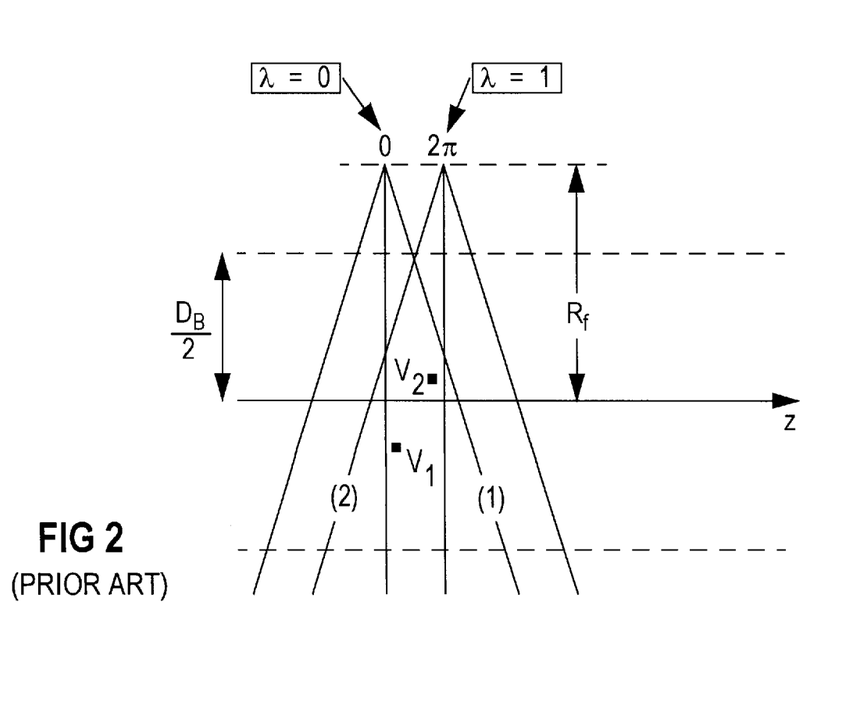

In the Wang algorithm, it must be ensured that each voxel of the reconstruction volume receives a back-projection contribution from all directions $x=0 \ldots 2\Pi$ of a full revolution. As mentioned above, for each index $n_0$ a revolution of the spiral is individually chosen for each voxel, from which turn the projection with the corresponding projection angle $\alpha_{n_0}$ is employed. The $\lambda(x,y,z,n_0)$ are selected so that the selected projection is always the one lying nearest the relevant voxel in the z direction. The situation is illustrated in FIG. 2. In the back-projection under the projection angle $\alpha_{n_0}=0$, for the voxel $V_1$, the value of $\lambda$ is chosen equal to 0, while in contrast $\lambda$ is chosen equal to 1 for the voxel $V_2$. Thus, for the back-projection into the voxel $V_1$, the projection shown at left is used, and for the back-projection into the voxel $V_2$, the projection shown at right is used, although for both voxels both projections would be possible.

The requirement that each voxel must receive back-projection contributions from all projection angles is the main disadvantage of the Wang algorithm. This requirement limits the pitch of the spiral, defined as the z-advance $\Delta z_{2\pi}$ of the spiral per $2\pi$ complete revolution of the gantry, normalized to the row distance of the detector rows $\Delta\zeta$ projected into the rotational center.

$$pitch = \frac{\Delta z_{2\pi}}{\Delta\zeta} \qquad (11)$$

FIG. 2 illustrates this pitch limitation. A voxel V at the edge of the image field, with diameter $D_B$, must receive contributions from all directions $x=0 \ldots 2\Pi$. For this, the pitch cannot become larger than is shown in FIG. 2. The pitch is thus at a maximum when the beams (1) and (2) intersect exactly at the edge of the image field. The maximum pitch thereby results at:

$$pitch_{\max} = \frac{R_f - \frac{D_B}{2}}{R_f}(N_{rows} - 1). \qquad (12)$$

For a particular gantry geometry, there results e.g. ($R_f$=570 mm, $R_d$=435 mm, $D_B$=500 mm):

| rows | 3 | 4 | 5 | 6 | 7 |
|---|---|---|---|---|---|
| pitch$_{\max}$ | 1.1228 | 1.6842 | 2.2456 | 2.8070 | 3.3684 |

Figure 3:
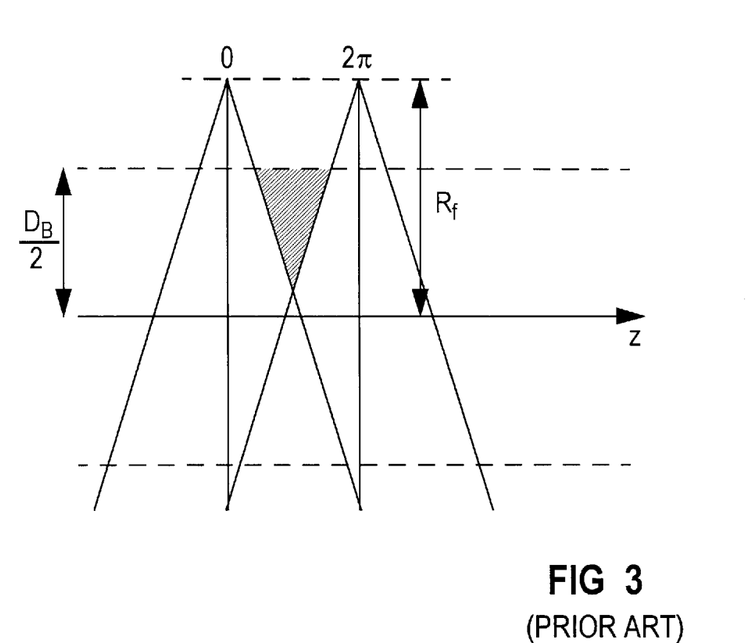

If the pitch of the spiral is increased above this critical value, gaps arise in the sampling scheme (see FIG. 3, shading). For these shaded gaps, there are no projections under certain projection angles x that could supply a contribution in these areas in the back-projection. The original Wang algorithm thus cannot be used for the reconstruction of spirals with such large pitch values. A pitch of 2.25 for a 5-row detector is however too small for a practically usable application.

A second disadvantage of the Wang algorithm is that the back-projection is carried out projection-by-projection. For each projection angle, the supplement of a projection to a voxel, which projection is recorded under this projection angle, is determined by interpolation between the elements of the convolved projection that are adjacent to the projection of the relevant voxel from the focus into the detector. Accordingly, the range of the interpolation in the z direction in the rotational center is $$\text{approximately } \Delta\zeta = \Delta\zeta_{Det}\frac{R_f}{R_f + R_d}.$$

SUMMARY OF THE INVENTION

An object of the invention is to provide a method for image reconstruction in a computed tomography apparatus having a multi-row detector and operable in a helical/spiral scan mode, of the general type described above, wherein the pitch limitation of the Wang algorithm is overcome, without having recourse to a partial revolution reconstruction that has other disadvantages, and an interpolation is enabled in the z direction with a smaller range, in order to increase the z resolution.

The above object is achieved in accordance with the principles of the present invention in a method for an image reconstruction in a multi-row detector computed tomography apparatus operable in a spiral/helical scan mode, the method being applicable for arbitrary pitch (i.e., advance along the z-axis per full revolution related to the layer width), wherein complementary fans are produced from the measured direct beam fans and a subsequent convolved fan back-projection is conducted including both the direct and complementary beam fans.

DESCRIPTION OF THE PREFERRED EMBODIMENTS

Figure 4:
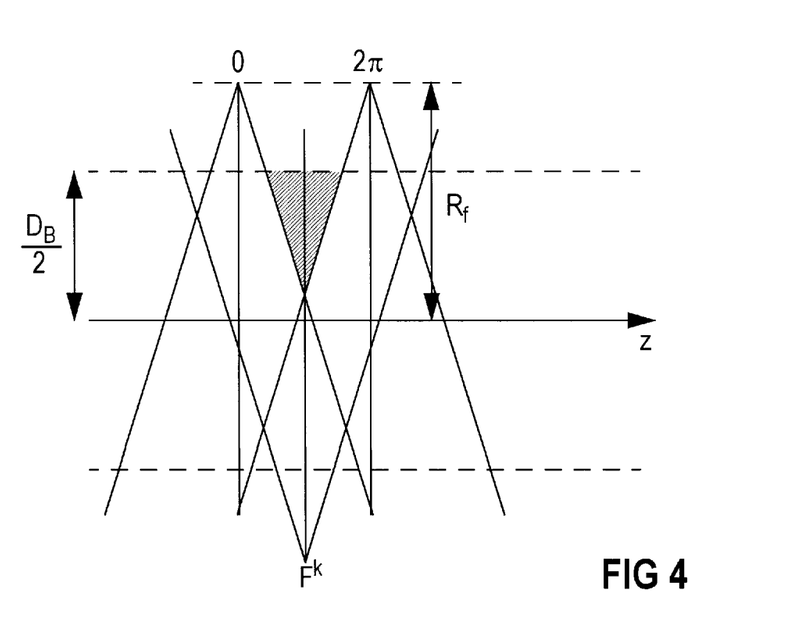
FIG. 4 illustrates a spiral scanning in a multi-row computer tomograph according to the invention, having large pitch.

The inventive method is based on the recognition that the gaps in FIG. 3 can be filled by beams measured from focus positions lying opposite (e.g. $F^k$ in FIG. 4). These beams, issuing from opposed focus positions, are called complementary beams. In contrast, the beams issuing from the focus positioned at the momentary projection angle $\alpha_{n_0}$ are called direct beams.

If no projection is available for the back-projection under the projection angle $\alpha$ in a particular area of the reconstruction volume (gaps in FIG. 4), then the complementary beams $p^k(\alpha,\beta,\xi_{Det,q})=$ $$p^k(\alpha, \beta, \xi_{Det,q}) = p(\tilde{\alpha}, \tilde{\beta}, \xi_{Det,\tilde{q}})$$

are used in place of the beams $p(\alpha,\beta,\xi_{Det,q})$, these complementary beams fulfilling the conditions $$\tilde{\beta} = -\beta, \quad (13)$$

$$\tilde{\alpha} + \tilde{\beta} = \alpha + \beta + \pi \quad (14)$$

In addition, the following is set:

$$\tilde{q} = q \quad (15)$$

Through grouping of all the complementary beams belonging to a fixed $\alpha$ but different $\beta$, so-called complementary fans $p^k(\alpha_n,\beta_m,\xi_{Det,q})$ are produced. While all beams of a direct fan converge in one point, the physical focus point, the beams of a complementary fan emanate from virtual focus points, which lie on a z-parallel line described by $$\vec{r}_{VF} = \begin{bmatrix} R_f \cos\alpha \\ R_f \sin\alpha \\ z_F^k(n, m, q) \end{bmatrix} \quad (16)$$

wherein $z^k_F$ is thereby the z coordinate of the respective virtual focus. It is noteworthy that in general each beam of such a projection has another virtual focus lying on this line. By means of the regrouping described above, the roles of the focus and the detector are exchanged. Thus, the sign for complementary projections in equation (2) must change. Equation (17) is an equation that holds for both types of projections.

By means of this grouping of the complementary beams, there arises in addition to the directly measured spiral of the multi-row detector a second spiral from complementary projection fans. These complementary fans are then treated for the reconstruction in the same way as the direct fans $p(\alpha_n,\beta_m,\xi_{Det,q})$; in particular, reconstruction step (5) is also used on these complementary fans.

In order to simplify the notation, from here on both direct and complementary fans will be designated with $p(n,m,q,c)$, whereby if $c=1$ this means a direct fan and complementary fans have $c=-1$.

In this formulation, equation (2) becomes $$\xi_{Det,q} = c \cdot \left( q - \frac{N_{rows}}{2} + 0.5 + AQ \right) \Delta \xi_{Det} \quad (17)$$

Since in practice discrete projections are present, angle positions for $\alpha$ and $\beta$ resulting from evaluation of equations (13) and (14) generally do not fall onto actually measured data. For this reason, the complementary fans must be obtained through interpolation. For this purpose, one proceeds as follows:

Let $$\alpha_{n1}{}^k = n_t \Delta \alpha \quad (18)$$

and $$\beta_{m1}{}^k = (m_t + 0.5 + AM^k)\Delta\beta \quad (19)$$

be the characteristic quantities of a complementary beam $p(n_t,m_t,q_t,c=-1)$ to be calculated (index t: target), and let $$\tilde{\alpha}_{\tilde{n}} = \tilde{n}\Delta\alpha \quad (20)$$

and $$\tilde{\beta}_{\tilde{m}} = (\tilde{m} + 0.5 + AM)\Delta\beta \quad (21)$$

be the characteristic quantities of a direct beam $p(\tilde{n},\tilde{m},\tilde{q},c=1)$, from which the complementary beam $p(n_t,m_t,q_t,c=-1)$ is to be calculated.

From (13) and (14), with the arbitrary stipulation $AM^k = AM$, there results:

$$\tilde{m} = -m_t - 1 - 2AM \quad (22)$$

and $$\tilde{n} = n_t + (2m_t + 1 + 2AM)\frac{\Delta\beta}{\Delta\alpha} + \frac{\pi}{\Delta\alpha} \quad (23)$$

This first yields non-integers $\tilde{n}$ and $\tilde{m}$. The complementary beam $p(n_t, m_t, q_t, -1)$ is now to be produced by means of interpolation from adjacent $(n \cdot \tilde{n}, m \cdot \tilde{m})$ beams with integral n and m, e.g. through bilinear interpolation between the adjacent beams.

The z positions of the produced complementary beams.

The z focus position of a direct beam in the spiral with slope slope=$_{d\alpha}^{dz_F}$ results as $$z_F(n) = z_{f,0} + n\Delta\alpha \cdot \text{slope}. \quad (24)$$

For a complementary beam, one obtains $$z_F^k(n, m, q) = z_{F,0} + \tilde{n}\Delta\alpha \cdot \text{slope} + 2R_f \cos\tilde{\beta}\tan\tau_q \quad (25)$$

wherein $T_q$ is the angle of inclination of a beam against a plane perpendicular to the z axis (known as the cone angle). The following holds:

$$\tan\tau_q = \frac{\xi q}{R_f} \quad (26)$$

$\tilde{n}$ and $\beta$ are given by (23) or (13).

$z^k_F$ is the z position of the virtual focus. $z^k_F$ can be partitioned into a constant part, an independent part and an m-dependent part. with (21), (22) and (23) there follows:

$$z_F^k(n, m, q) = z_{F,0} + \left[n + (2m + 1 + 2AM)\frac{\Delta\beta}{\Delta\alpha}\right]\Delta\alpha \cdot \text{slope} + \quad (27)$$

$$2R_f \cos\left[-(m + 0.5 + AM)\Delta\beta\right]\tan\tau_q$$

$$= z_{F,0} + [(1 + 2AM)\Delta\beta + \pi] \cdot \text{slope} + \quad \text{(constant)}$$

$$2m\Delta\beta \cdot \text{slope} + 2R_f \cos\left[(m + 0.5 + AM)\Delta\beta\right]\tan\tau_q + \quad \text{(m-dependent)}$$

$$n\Delta\alpha \cdot \text{slope} \quad \text{(n-dependent)}$$

The m-dependent portion can be stored in the computer in a table.

The inclination of the complementary beams changes sign in relation to the corresponding direct ones, because the orientation changes due to the change of the roles of the focus and detector:

$$\tau_q^k = -\tau_q \quad (28)$$

Index Range of the Producible Complementary Beams

If the presence of direct projections for the index regions $$\tilde{m} = -\frac{N}{2} \ldots \left(\frac{N}{2} - 1\right), \tilde{n} = 0 \ldots (N_P - 1)$$

is assumed, then the index region of the complementary projections that can be produced therefrom is determined by a) $\quad m = \left[\frac{N}{2} \ldots \left(\frac{N}{2} - 1\right)\right] - 2AM,$ (from 22)

b) $\quad m \geq \frac{1}{2}\left[-n\frac{\Delta\alpha}{\Delta\alpha} - \frac{\pi}{\Delta\beta} - 1 - 2AM\right]$ (from 23)

c) $\quad m \geq \frac{1}{2}\left[(N_P - 1 - n)\frac{\Delta\alpha}{\Delta\beta} - \frac{\pi}{\Delta\beta} - 1 - 2AM\right]$ (from 23)

Sequence of the Reconstruction Algorithm

After the production of the complementary fans $p(n,m,q, c=-1)$, direct and complementary fans are weighted and convolved according to $$\tilde{p}(n, m, q, c) = \frac{1}{R_f \Delta\beta}\sum_{m'=-N/2}^{N/2-1} g_{m-m'}\frac{R_f}{\sqrt{R_f^2 + \zeta_q^2}}\cos\beta_{m'}p(n, m', q, c). \quad (29)$$

The convolved projections are subsequently back-projected over the projection angle region $2\Pi$, i.e. $n_0=0\ldots (N_{P,2\pi}-1)$. In addition, for each $n_0$ the following is first calculated for each voxel:

$$\hat{m}(x, y, z, n_0) = \frac{1}{\Delta\beta}\text{atan}\left(\frac{-x\sin\alpha_{n_0} + y\cos\alpha_{n_0}}{R_f + x\cos\alpha_{n_0} + y\sin\alpha_{n_0}}\right) - 0.5 - AM \quad (30)$$

Figure 5:
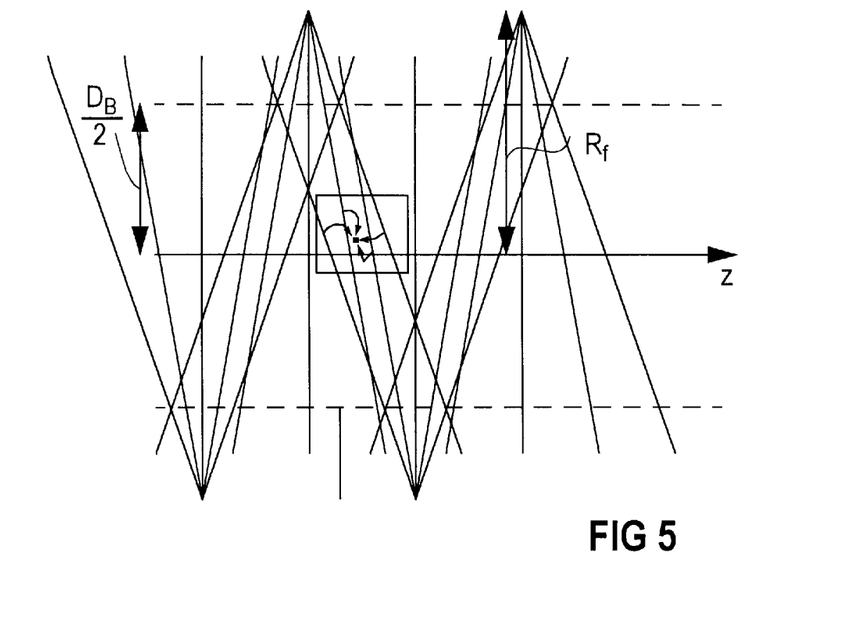
FIG. 5 illustrates the obtaining of a back-projection supplement by means of interpolation between the beams of the respective projection that are adjacent to the relevant voxel in a computer tomograph according to the invention.
Figure 6:
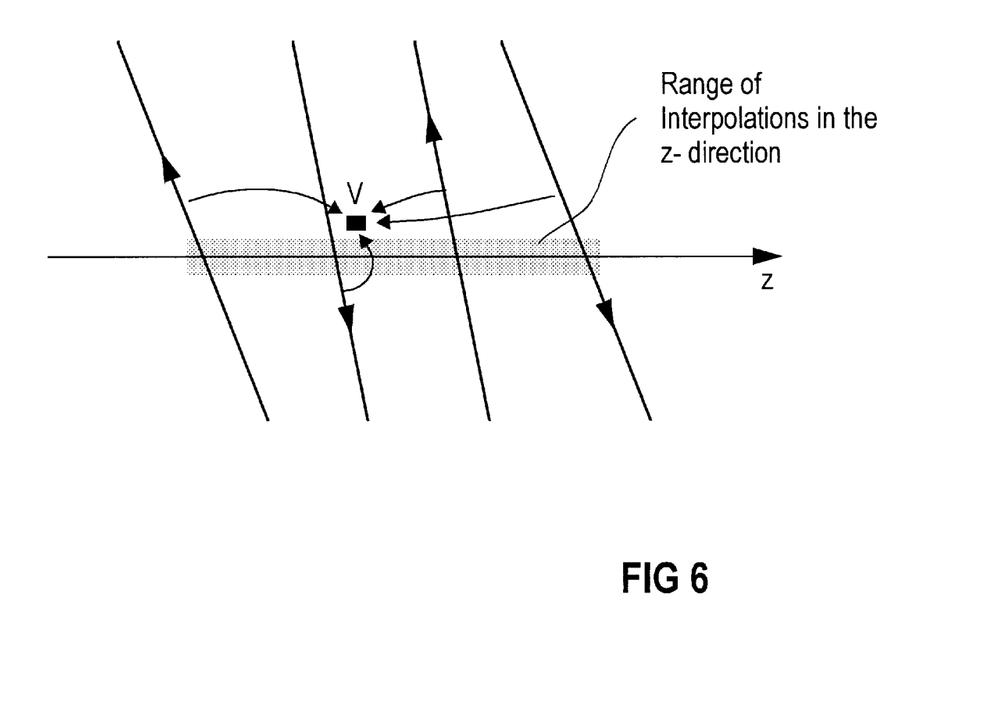
FIG. 6 illustrates an excerpt according to FIG. 5 and the interpolation with the Wang algorithm.
Figure 7:
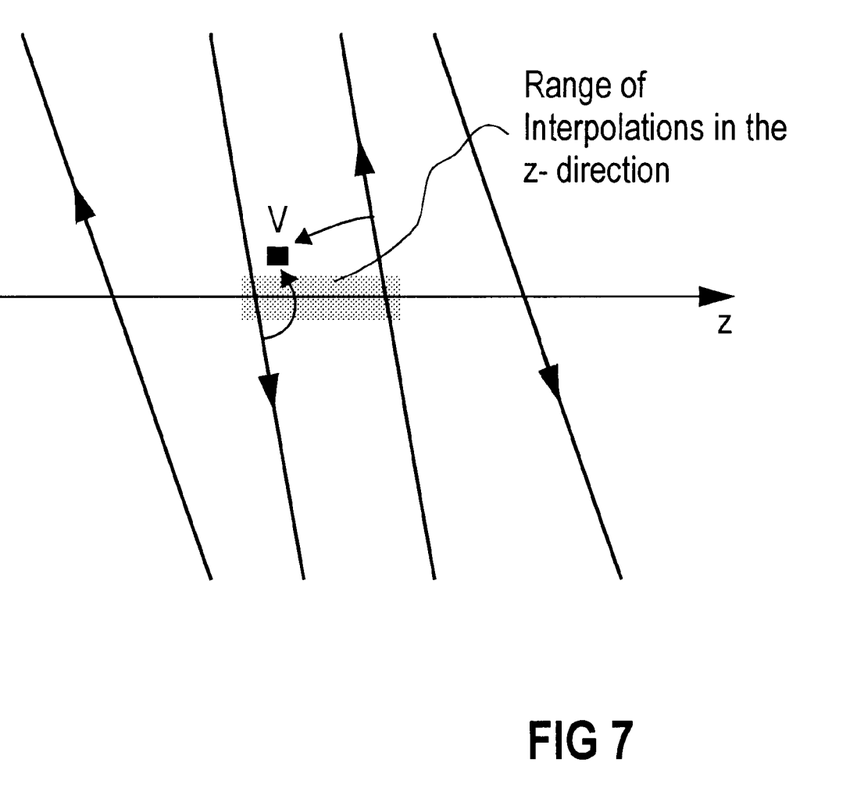
FIG. 7 illustrates an excerpt according to FIG. 5 and the interpolation with the inventive algorithm.

There results an $\hat{m}$ that is non-integer in the general case. The contribution to the voxel $V(x,y,z)$ must be calculated by means of interpolation between the adjacent beams with the indices $m \approx \hat{m}$. In contrast to the Wang algorithm, for each projection angle both the direct and the complementary fans are now thereby taken into account. From all the beams m m of the direct and the complementary fans, for a respective fixed m those beams are chosen that come the closest to the voxel to be reconstructed in the z direction. The back-projection contribution for the voxel V(x,y,z) is then obtained from the corresponding elements of the convoluted projections. A comparison of FIGS. 6 and 7 shows clearly that, under some circumstances, with the use of the Wang algorithm the range of the interpolations to be carried out in the z direction is greater than in the inventive method described herein. The inventive method can achieve a higher resolution in the z direction with the use of interlaced sampling schemes (as in FIG. 5). In addition, the requirement made in the Wang algorithm, that a voxel of the reconstruction volume must always be contained in at least one direct fan, is not made in the method presented. Thus, by means of the inclusion of both the direct and the complementary fans, not only can the pitch be increased but also the z resolution can be increased.

Increasing the z Resolution Using the Algorithm Presented

The Wang algorithm works projection-by-projection, i.e. one convolved projection after the other is back-projected into the reconstruction volume. The contribution to a voxel is thereby obtained by means of interpolation between different elements inside a projection. The interpolation required in the z direction thereby has a range of about $$\Delta \zeta = \Delta \zeta_{Det} \frac{R_f}{R_f + R_d}$$

in the vicinity of the rotational center. The situation is illustrated in FIGS. 5 and 6. In the new reconstruction method presented here, back-projection contributions are obtained by means of interpolation also between different projections. Both the direct and the complementary fans are included. In this way, if suitable scanning has taken place along the z direction, measurement beams can be found whose distance from the voxel in the center is smaller than $\Delta \xi$. If the back-projection contribution is obtained by means of interpolation from the elements of the convoluted projections corresponding to these beams, the z resolution is increased in relation to the Wang algorithm. To exploit this characteristic in practice, the pitch is set so that an interlaced sampling scheme results along the z direction in which the beams of respectively opposite focus positions mesh in the vicinity of the rotational center (as in FIG. 5).

Omission of Pitch Limitation with the Presented Algorithm

In the Wang algorithm, the pitch is limited by the requirement that among all the projection angles for each voxel there is at least one projection in which bundle of rays the voxel is located. When the pitch is enlarged, gaps, for which this requirement is not fulfilled, arise in the reconstruction region (shaded in FIG. 3). As can be seen in FIG. 4, however, the beams emanating from the opposite focus position can be used. With this procedure, the algorithm presented herein achieves a reconstruction for arbitrary pitch. If no directly measured projection containing the relevant voxel is present, the complementary projection is used instead. Generally stated, the beams either of the direct or of the complementary projections are always used that have the smallest distance in the z direction from the relevant voxel.

Figure 8:
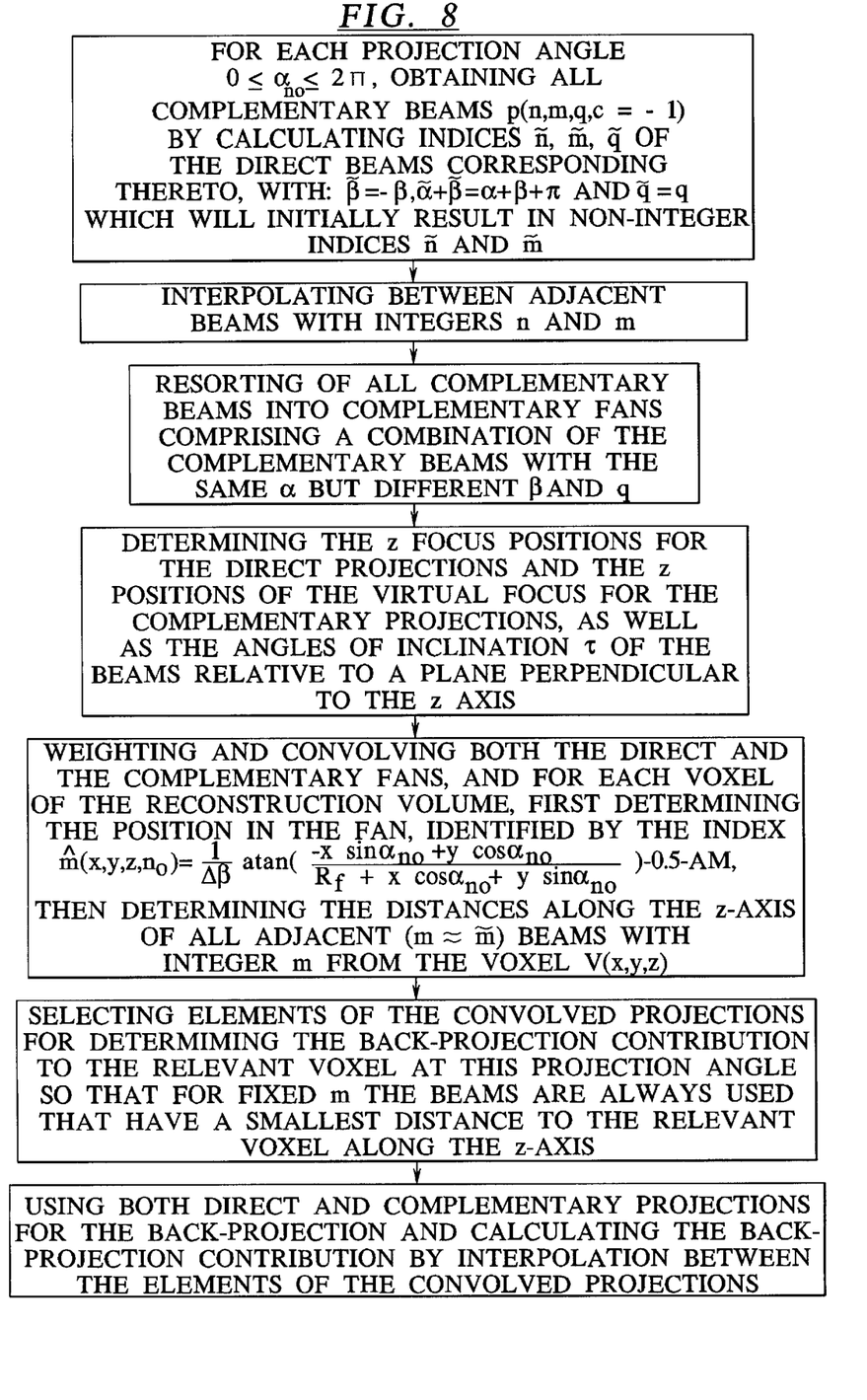
FIG. 8 is a flowchart illustrating the inventive Algorithm.

The above described steps are summarized in the flowchart of FIG. 8.

Special Case of Bilinear Interpolation

The following is a somewhat more detailed treatment of the special case of bilinear interpolation.

With $\hat{m}$ according to (30), $m_{lo}$=floor($\hat{m}$) and $m_{hi}$=ceil($\hat{m}$). For the direct and complementary beams with the indices ($n_0 + \lambda N_{P,2\pi}$, $m_{lo}$) and ($n_0 + \lambda N_{P,2\pi}$, $m_{hi}$), the distances $d_z$ of the beams $m=m_{lo}$ and $m=m_{hi}$ are calculated for the particular voxel to be processed. There results:

$$d_z = z_f + \tan \tau_q \sqrt{(R_f + x\cos\alpha_{n_0} + y\sin\alpha_{n_0}^2 + (-x\sin\alpha_{n_0} + y\cos\alpha_{n_0})^2} - z \quad (30)$$

for the direct beams, and $$d_z = z_{ff}^k + \tan \tau_q^k \sqrt{(R_f + x\cos\alpha_{n_0} + y\sin\alpha_{n_0}^2 + (-x\sin\alpha_{n_0} + y\cos\alpha_{n_0})^2} - z \quad (31)$$

for the complementary beams. The indices ($\lambda_{lo,down}$, $q_{lo,down}$, $c_{lo,down}$) and ($\lambda_{lo,up}$, $q_{lo,up}$, $c_{lo,up}$) are now selected so that the associated $d_z$ has the largest negative value or the smallest positive value among all the possibilities with $m=m_{lo}$. Likewise, ($\lambda_{hi,down}$, $q_{hi,down}$, $c_{hi,down}$) and ($\lambda_{hi,up}$, $q_{hi,up}$, $c_{hi,up}$) are chosen so that the associated $d_z$ has the largest negative value or the smallest positive value among all possibilities with $m=m_{hi}$. Finally, the contribution of the back-projection from the projection angle $\alpha_{n_0}$ to the relevant voxel is determined by means of bilinear interpolation from the four values $$\tilde{p}_{00} = \tilde{p}(n_0 + \lambda_{lo,down} N_{P,2\pi}, m_{lo}, q_{lo,down}, c_{lo,down}), \quad (32)$$

$$\tilde{p}_{01} = \tilde{p}(n_0 + \lambda_{lo,up} N_{P,2\pi}, m_{lo}, q_{lo,up}, c_{lo,up}), \quad (33)$$

$$\tilde{p}_{10} = \tilde{p}(n_0 + \lambda_{hi,down} N_{P,2\pi}, m_{hi}, q_{hi,down}, c_{hi,down}), \quad (34)$$

$$\tilde{p}_{11} = \tilde{p}(n_0 + \lambda_{hi,up} N_{P,2\pi}, m_{hi}, q_{hi,up}, c_{hi,up}), \quad (35)$$

These results $$\tilde{P}_{acc} = \frac{m_{hi} - \hat{m}}{-d_z(\lambda_{lo,down}, q_{lo,down}, c_{lo,down}) + d_z(\lambda_{lo,up}, q_{lo,up}, c_{lo,up})} \cdot$$

$$\left[ d_z(\lambda_{lo,up}, q_{lo,up}, c_{lo,up}) \tilde{P}_{00} - d_z(\lambda_{lo,down}, q_{lo,down}, c_{lo,down}) \tilde{P}_{01} \right] +$$

$$\frac{\hat{m} - m_{lo}}{-d_z(\lambda_{hi,down}, q_{hi,down}, c_{hi,down}) + d_z(\lambda_{hi,up}, q_{hi,up}, c_{hi,up})} \left[ d_z(\lambda_{hi,up}, q_{hi,up}, c_{hi,up}) \tilde{P}_{10} - d_z(\lambda_{hi,down}, q_{hi,down}, c_{hi,down}) \tilde{P}_{11} \right]$$

The reconstruction is finished when the back-projection contributions for all projection angles $\alpha_{n_0}$ have been added to all voxels.

The specified method is thereby suited for arbitrary pitches, and is additionally suited to increase the z resolution, given interlaced sampling.

The specified method enables spiral reconstruction with arbitrary pitch while also improving the z resolution for interlaced sample schemes.

Although modifications and changes may be suggested by those skilled in the art, it is the intention of the inventors to embody within the patent warranted hereon all changes and modifications as reasonably and properly come within the scope of their contribution to the art.

We claim as our invention:

1. Method for image reconstruction for a computed tomography apparatus in a spiral/helical scan for arbitrary advance along a z-axis per full revolution related to a slice width, said computed tomography apparatus having a radiation source which emits a fan beam having a beam angle $\beta$ and an alignment AM from a focus which proceeds on a spiral focus path having a radius $R_f$, and a multi-row radiation detector wherein q is a row index, said method comprising the steps of producing complementary fans p(n,m,q,c) wherein c=−1 from measured direct beam fans p(n,m,q,c=1), and subsequent convolved fan back-projection including both the direct beam fans and the complementary fans, by, for each projection angle $0 \leq \alpha_{n_0} \leq 2\pi$, obtaining all complementary beams p(n,m,q, c=−1) by calculating indices $\tilde{n}$, $\tilde{m}$, $\tilde{q}$ of the direct beams corresponding thereto, with: $\tilde{\beta}=-\beta, \alpha+\tilde{\beta}=\alpha+\beta+\pi$ and $\tilde{q}=q$ which will initially result in non-integer indices n and $\tilde{m}$ and by subsequently interpolating between adjacent beams with integers n and m, and resorting of all complementary beams into complementary fans comprising a combination of the complementary beams with the same $\alpha$ but different $\beta$ and q, determining the z focus positions for the direct projections and the z positions of the virtual focus for the complementary projections, as well as the angles of inclination $\tau$ of the beams relative to a plane perpendicular to the z axis, then weighting and convolving both the direct and the complementary fans, and for each voxel of the reconstruction volume, first determining the position in the fan, identified by the index $$\hat{m}(x, y, z, n_0) = \frac{1}{\Delta\beta} a\tan\left(\frac{x\sin\alpha_{n_0} + y\cos\alpha_{n_0}}{R_f + x\cos\alpha_{n_0} + y\sin\alpha_{n_0}}\right)$$

−0.5−AM, then determining the distances along the z-axis of all adjacent (m≈m̃) beams with integer m from the voxel V(x,y,z), selecting elements of the convolved projections for determining the back-projection contribution to the relevant voxel at this projection angle so that for fixed m the beams are always used that have a smallest distance to the relevant voxel along the z-axis, and using both direct and complementary projections for the back-projection and calculating the back-projection contribution by interpolation between the elements of the convolved projections.

* * * * *